United States Patent [19]

Selwitz et al.

[11] 4,175,210

[45] Nov. 20, 1979

[54] ETHERIFICATION PROCESS

[75] Inventors: Charles M. Selwitz, Monroeville; John G. McNulty, Glenshaw, both of Pa.

[73] Assignee: Gulf Research and Development Company, Pittsburgh, Pa.

[21] Appl. No.: 916,969

[22] Filed: Jun. 19, 1978

[51] Int. Cl.$^2$ ............................................. C07C 41/06
[52] U.S. Cl. .................................. 568/689; 568/697; 568/579
[58] Field of Search ...................... 260/614 A, 611 R; 568/689, 697, 695, 579, 901

[56] References Cited

U.S. PATENT DOCUMENTS

| 2,067,385 | 1/1937 | Evans et al. | 260/614 A |
| 2,702,232 | 2/1955 | Arnold et al. | 260/614 A X |

FOREIGN PATENT DOCUMENTS

| 2022568 | 1/1973 | Fed. Rep. of Germany | 568/901 |
| 47-30608 | 9/1972 | Japan | 568/901 |

Primary Examiner—Bernard Helfin

[57] ABSTRACT

A process for converting an olefin, or a mixture of olefins, to an ether, or a mixture of ethers, which comprises reacting said olefin, or said mixture of olefins, with an alcohol in contact with silicatungstic acid.

15 Claims, No Drawings

ETHERIFICATION PROCESS

BACKGROUND OF THE INVENTION

1. Field of the Invention

This invention relates to a new and useful process for converting an olefin, or a mixture of olefins, to an ether, or a mixture of ethers, which comprises reacting said olefin, or said mixture of olefins, with an alcohol, or a mixture of alcohols, in contact with silicatungstic acid.

2. Description of the Prior Art

Present commercial methods for reacting an olefin with an alcohol to obtain an ether involve the use of a mineral acid catalyst, such as, for example, sulfuric acid. Unfortunately, such methods have a number of disadvantages. These can include, for example, severe corrosion, acid-handling difficulties, high loss of acid, and the costly step of reconcentrating a diluted acid. More significantly, these methods, being used primarily to convert branched olefins to ethers, do not readily convert a mixture of olefins and, in particular, the unbranched and cyclic olefins to ethers. Consequently, a need exists for a simple, economical process for converting all classes of olefins, or a mixture of olefins, to ethers. Accordingly, the present invention provides a process for converting an olefin, or a mixture of olefins, to an ether, or a mixture of ethers, which comprises reacting said olefin, or said mixture of olefins, with an alcohol in contact with silicatungstic acid.

SUMMARY OF INVENTION

We have discovered a novel process for converting an olefin, or a mixture of olefins, to an ether or a mixture of ethers which comprises reacting said olefin, or said mixture of olefins, with an alcohol, or a mixture of alcohols, in contact with silicatungstic acid.

DETAILED DESCRIPTION OF THE PROCESS

Any olefin, or a mixture of olefins, is suitable for use in the present invention. In general, olefins are unsaturated aliphatic hydrocarbons containing one or more double bonds, and, hence, are chemically reactive. Those olefins containing one double bond are called alkenes and have the general formula $C_nH_{2n}$, and those with two double bonds are referred to as alkadienes or diolefins and have the general formula $C_nH_{2n-2}$. Both olefins and diolefins can be unbranched, branched or cyclic and are suitable in the present invention and referred to as, simply, "olefin" herein. Especially suitable olefins for use in the present invention have from about 3 to about 14 carbon atoms, preferably from about 4 to about 10 carbon atoms. By unbranched olefin is meant an unsaturated hydrocarbon of the structure:

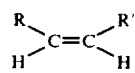

where R and R' are a hydrogen, a straight chain alkyl group, or a straight chain alkenyl group containing from about 1 to about 12 carbon atoms, preferably from about 1 to about 8 carbon atoms, but no more than one of these can be a hydrogen. By branched olefin is meant an unsaturated hydrocarbon of the structure:

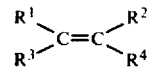

where $R^1$, $R^2$, and $R^3$ are hydrogen, alkyl or alkenyl groups containing from about 1 to about 10 carbon atoms, preferably about 1 to about 8 carbon atoms, and $R^4$ is an alkyl or alkenyl group containing from about 1 to about 10, preferably about 1 to about 8 carbon atoms. By a cyclic olefin is meant a cyclic unsaturated hydrocarbon with the unsaturation in the ring. Any cyclic olefin is suitable for use herein. Cyclic olefins for use herein can have from about 5 to about 20 carbon atoms, preferably from about 5 to about 14. Unbranched olefins work especially well in the present invention and are the olefins of preference. Unbranched olefins can include, for example, 1-butene, 1-octene, 1-hexene and 1-dodecene; hexene-2; hexene-3; decene-4. Branched olefins can include, for example, isobutylene, 2-methylpentene-2, 2-methyl butene-2, and 2,3-dimethyl octene-2. Diolefins suitable for use in the present invention can include, for example, piperylene and isoprene. Cyclic olefins can include, for example, cyclopentene and methycyclopentene. Cyclic diolefins can include, for example, cyclopentadiene and dicyclopentadiene.

Any alcohol, or mixture of alcohols, is suitable for use in the present invention. In general, an alcohol is a class of hydroxyl-containing compounds having the generic formula $C_nH_{2n+1}OH$ for alcohol derivatives of saturated hydrocarbons. There are also alcohols of unsaturated hydrocarbons which can be used in the invention herein. Alcohols may be mono-, di-, or trihydric according to the number of hydroxyl radicals they contain, and primary, secondary, or tertiary according to the number of hydrogen atoms attached to the carbon atom adjacent to the OH group. Especially suitable alcohols for use in the present invention contain 1 to 3 carbon atoms, preferably 1 to 2 carbon atoms, for example, methanol, ethanol, and propanol, with the most preferred alcohol being methanol. Of course, mixtures of these enumerated alcohols can be used herein.

The alcohol can be mixed with the olefin in the present invention in any molar ratio. In general, the molar ratio of alcohol-to-olefin ranges from about 1:1 to about 15:1, preferably from about 2:1 to about 5:1.

The silicatungstic acid used as a catalyst herein is old and well-known and can be defined by the formula $SiO_2.12WO_3$. A description of a typical preparation of silicatungstic acid is set forth, for example, in U.S. Pat. No. 3,361,518. The preparation of the deposition of silicatungstic acid on a silica is described, for example, in U.S. Pat. No. 2,982,799. In general, the weight percentage of silicatungstic acid relative to silica in the catalyst is about 5 to about 100 percent, preferably about 30 to about 100 percent.

The present invention preferably employs a fixed bed of catalyst with olefin and alcohol passing through the catalyst bed in the vapor phase to yield a product in a direct, one-stage process. However, the present invention can be carried out as a batch operation. The liquid hourly space velocity (LHSV) of the present invention is not critical, but, in general, ranges from about 0.02 to about 2, preferably about 0.1 to about 0.5 volume of feed per volume of catalyst per hour (vol feed/vol cat/hr).

The temperature of the process of the present invention is not critical. In general, the temperature ranges from about 50 to about 200° C., preferably from about 80° to about 120° C.

In the present invention the preferred pressure is atmospheric pressure (ambient pressure), but the pressure can range from about 0.1 to about 10 atmospheres, (9.646 to about 964.6 kPa) or even higher.

In general, this product is a mixture of unreacted alcohol, unreacted olefin, the desired ether, and dimethyl ether. The liquid product is removed from the solid catalyst by filtration or by percolation. The desired ether is separated from the remaining product by any suitable procedure, but preferably by distillation at ambient pressure. Unreacted alcohol and olefin are recovered by distillation and can be recycled.

DESCRIPTION OF PREFERRED EMBODIMENTS

The invention will be further described with reference to the experimental data.

The supported catalyst used in the experiments was prepared as follows:

Silicatungstic acid, purchased from Fisher Scientific, was dissolved in water to provide 422.9 grams of solution containing 21.82 percent $SiO_2.12WO_3$. The support was 215.3 grams of Davison silica gel, $SiO_2$, grade 70, 10–20 mesh which had been calcined at 1000° F. for 10 hours. The support and solution were mixed to give 638.2 grams, net weight, of powder and this was dried at 250° F. for 24 hours to give 310 grams of dry product. This product was calcined at 752° F. for 16 hours to give the catalyst, 30 percent silicatungstic acid on silica gel.

EXAMPLE 1

Octene-1 and methanol in a 15:1 alcohol-to-olefin molar ratio was combined with 3.4 weight percent of sulfuric acid in a liquid phase batch reactor and agitated for 3 hours at 117° C. and 861.25 kPa (125 psig) pressure.

The product was distilled to obtain the desired ether which was analyzed by gas chromatography using a 10-foot 20 percent silicone (fluoro) QF-1 (FS-126S) column programmed from 50° to 195° C. The conversion to the desired ether was 7.2 mole percent according to the following calculation:

$$\frac{\% \text{ desired ether/mol wt}}{\% \text{ olefin/mol wt} + \% \text{ desired ether/mol wt}} = \text{mole } \% \text{ conversion}$$

This run is identified as Run No. 1 in Table 1.

Run Nos. 2 through 5 were prepared identically to Example 1, except with the changes as set forth in Table 1.

EXAMPLE 2

Fifty milliliters of 30% $SiO_2.12WO_3$ were charged to a 210-ml glass reactor. The remaining volume of the reactor was filled with Raschig rings as a preheat section. The reactor was placed in an electrical resistance furnace. Methanol and octene-1 mixed in a 2.5 to 1 molar ratio were passed downflow over the catalyst at a LHSV of 0.4. The temperature of the catalyst bed was kept between 98°–107° C.

The product was filtered to remove traces of catalyst. The liquid was distilled to obtain the desired ether which was analyzed by gas chromatography using a 10-foot 20 percent silicone (fluoro) QF-1 (FS-126S) column programmed from 50° to 195° C. The conversion of octene-1 to methyl octyl ether was 12.7 mole percent according to the following calculation:

$$\frac{\% \text{ methyl ether/mol wt}}{\% \text{ olefin/mol wt} + \% \text{ methyl ether/mol wt}} = \text{mole } \% \text{ conversion}$$

This run is identified as Run No. 8 in Table 2.

EXAMPLE 3

The same equipment as used in Example 1 was employed, except that methanol and hexene-1 in a 2.5 to 1 molar ratio were charged over a catalyst bed controlled at a temperature between 99°–101° C. at a LHSV of 0.16.

Analysis of the product by the same procedures as employed in Example 1 gave a 20.1 mole percent conversion of hexene-1 to methyl-hexyl ether. This run is identified as Run No. 9 in Table 2.

Run Nos. 6 through 11 were prepared identically to Example 2, except with the changes as set forth in Table 2.

Table 1

Liquid Phase Batch Reduction with Various Catalysts

| Run No. | Olefin | Catalyst Type | Catalyst Wt % | Time, hr | Temperature, °C. | Pressure, kPa (psig) | $CH_3OCH_3$ | Unreacted $CH_3OH$ | Unreacted Olefin | Desired Ether | Mole Conversion to Ether |
|---|---|---|---|---|---|---|---|---|---|---|---|
| 1 | Octene-1 | $H_2SO_4$ | 3.4 | 3 | 117 | 861.25(1-25) | * | * | 91.1 | 8.9 | 7.2 |
| 2 | Octene-1 | $BF_3$ | 2.9 | 3 | 127 | 943.93(1-37) | * | * | 98.7 | 1.3 | 1.0 |
| 3 | Octene-1 | p-Toluene Sulfonic | 6.0 | 3 | 127 | 999.05(1-45) | 4.8 | 78.6 | 15.4 | 1.2 | 5.8 |
| 4 | Hexene-1 | $H_2SO_4$ | 3.2 | 3 | 110 | 785.46(1-14) | 3.1 | 79.9 | 16.5 | .5 | 2.2 |
| 5 | Hexene-1 | $H_2SO_4$ | 3.2 | 3 | 128 | 1171.3(17-0) 7.0 | 68.9 | 22.4 | 1.7 | 5.3 | |

*not determined

Table 2

Fixed Bed Continuous Reaction of Solid Catalysts**

| | | | | | Pressure, | Product Analysis, wt % | | | | Mole % |
| Run No. | Olefin | Catalyst, wt % | LHSV | Temperature, °C. | kPa (psig) | $CH_3OCH_3$ | Unreacted $CH_3OH$ | Unreacted Olefin | Desired Ether | Conversion to Ether |
|---|---|---|---|---|---|---|---|---|---|---|
| 6 | Octene-1 | Triple A | 0.28 | 145 | Ambient | * | 30.8 | 60.3 | 8.9 | 10.5 |
| 7 | Octene-1 | 4% W, 8% Mo on $Al_2O_3$ | 0.2 | 170–175 | Ambient | 3.4 | 7.7 | 82.1 | 6.8 | 6.1 |
| 8 | Octene-1 | 30% $SiO_2 . 12WO_3$ on silica | 0.4 | 98–107 | Ambient | 1.2 | 57.9 | 34.5 | 6.4 | 12.7 |
| 9 | Hexene-1 | 30% $SiO_2 . 12WO_3$ on silica | 0.16 | 99–101 | Ambient | 1.9 | 45.5 | 39.2 | 13.4 | 20.1 |
| 10 | Hexene-1 | 30% $SiO_2 . 12WO_3$ on silica | 0.24 | 105–109 | Ambient | 2.4 | 46.7 | 39.4 | 11.5 | 17.2 |
| 11 | Mixed Hexene-2 and Hexene-3 | 30% $SiO_2 . 12WO_3$ on silica | 0.72 | 110–112 | Ambient | 1.2 | 31.6 | 57.1 | 10.1 | 11.3 |

**All runs use a 2.5:1 molar ratio of methanol to olefin.

In Tables 1 and 2 it is shown that for unbranched olefins having a double bond on a terminal carbon atom, silicatungstic acid is superior to protonic acids. This is shown by a comparison of Run Nos. 1, 4 and 5 using sulfuric acid and Run No. 3 using para-toluene sulfuric acid in Table 1 with Run Nos. 8 through 10 using silicatungstic acid on silica in Table 2. The sulfuric acid runs had a mole percent conversion to ether of only 2.2 to 7.2, while the silicatungstic acid runs had a mole percent conversion to ether ranging from 12.7 to 20.1. Run No. 2 in Table 1 shows that a Lewis acid, $BF_3$, was ineffective and had only a 1 mole percent conversion. That silicatungstic acid (Run Nos. 8, 9 and 10, having mole percent conversions of 12.7, 20.1, and 17.2, respectively is unique among heterogeneous phase acid catalysts is shown by a comparison with Triple A grade silica-alumina (Run No. 6, having a mole percent conversion of 10.5 and with 4 percent tungsten and 8 percent molybdenum on alumina (Run No. 7, having a mole per-cent conversion of 6.1). The ability of silicatungstic acid to catalyze the addition of alcohols to unbranched olefins having double bonds on carbon atoms other than the terminal carbon atom is demonstrated by Run No. 11 in Table 2 in which a mixture of hexene-2 and hexene-3 was reacted to give a mole percent conversion of 11.3.

EXAMPLE 4

2-Methyl-butene-2 was combined with methanol in a 2.5 alcohol-to-olefin molar ratio. The mixture was combined with 30% $SiO_2.12WO_3$ on silica (6.2 grams per 61.6 grams of solution) in a liquid phase batch reactor and agitated for 1 hour at 113° C. and 275.6 kPa (40 psig) pressure.

The product was distilled to obtain the desired ether which was analyzed by gas chromatography using a 10-foot 20 percent silicone (fluoro) QF-1 (FS-1265) column programmed from 50° to 195° C. The conversion to the desired ether was 50 mole percent.

This run is identified as Run No. 12 in Table 3.

Run Nos. 13 through 15 were prepared identically to Example 4, except with the changes as set forth in Table 3.

Table 3

Batch Liquid Phase Reactions with Silicatungstic Acid

| | | Alcohol/ Olefin Molar Ratio | | | | Pressure, | Product Analysis, wt % | | | | Mole % |
| Run No. | Olefin | | Catalyst | Time, hr | Temperature °C. | kPa (psig) | $CH_3OCH_3$ | Unreacted $CH_3OH$ | Unreacted Olefin | Desired Ether | Conversion to Ether |
|---|---|---|---|---|---|---|---|---|---|---|---|
| 12 | 2-methyl-butene-2 | 2.5 | 30% $SiO_2 . 12WO_3$ (6.2 grams per 61.6 grams of solution) | 1.0 | 113 | 275.6(40) | 1.2 | 54.5 | 18.2 | 26.1 | 50 |
| 13 | 1,3-pentadiene | 3.2 | unsupported $SiO_2 . 12WO_3 . 26H_2O$ (12.3 grams per 66 grams of solution) | 1.0 | 85–92 | 275.6(40) | 2.7 | 69.9 | 16.7 | 6.9 | 22 |
| 14 | 1,3-pentadiene | 3.2 | unsupported $SiO_2 . 12WO_3 . 26H_2O$ (6.0 grams per 60 grams of solution) | 1.0<br>1.0 | 67–71<br>90–93 | 275.6(40)<br>275.6(40) | 1.1<br>1.7 | 67<br>65.3 | 25<br>5.1 | 3.0<br>8.5 | 8<br>23 |
| 15 | hexene-1 | 2.5 | unsupported $SiO_2 . 12WO_3 . 26H_2O$ (6.0 grams per 60 grams of solution) | 2.0 | 110–123 | 275.6(40) | 0.3<br>4.7 | 40.2<br>77.6 | 55.3<br>19.4 | 4.2<br>1.3 | 5[1] |

[1]Two layers resulted in this run.

The runs set forth in Table 3 show the effect of varying the type of olefin on the process of the present invention. Run No. 12 shows that a branched olefin having a double bond and reacted with supported silicatungstic acid had a mole percent conversion of 50. Run No. 13 showed that a diolefin, 1,3-pentadiene, with pure, unsupported silicatungstic acid and an alcohol to olefin molar ratio of 3.2 had an acceptable mole percent conversion of 22, Run No. 14 showed that using a diolefin, 1,3-pentadiene, with silicatungstic acid in a batch system that there was a 8 mole percent conversion after 1 hour at 67°–71° C. while heating an additional hour at 90°–93° C. brought the conversion level to 23 mole percent.

Obviously, many modifications and variations of the invention, as hereinabove set forth, can be made without departing from the spirit and scope thereof, and therefore only such limitations should be imposed as are indicated in the appended claims.

We claim:

1. A process for converting an unbranched olefin having from about 3 to about 14 carbon atoms or a mixture of unbranched olefins, having an unsaturated hydrocarbon structure:

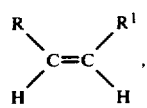

wherein R and $R^1$ and a hydrogen, a straight chain alkyl group or a straight chain alkenyl group containing from about 1 to about 12 carbon atoms but no more than one of said R and $R^1$ can be hydrogen, to an ether, or a mixture of ethers, which comprises passing a hydrocarbon alcohol and said olefin, or mixture of olefins, in a molar ratio of about 1:1 to about 15:1 in the vapor phase through a catalyst bed of silicatungstic acid at a liquid hourly space velocity of about 0.02 to about 2 volume of feed per volume of catalyst per hour at a temperature of about 50° to about 200° C. and a pressure of about 0.1 to about 10 atmospheres.

2. A process according to claim 1 wherein said olefin has from about 4 to about 10 carbon atoms.

3. A process according to claim 1 wherein said alkyl and said alkenyl groups contain from about 1 to about 8 carbon atoms.

4. A process according to claim 1 wherein said alcohol contains from 1 to 3 carbon atoms.

5. A process according to claim 1 wherein said alcohol contains 1 to 2 carbon atoms.

6. A process according to claim 1 wherein said alcohol is methanol.

7. A process according to claim 1 wherein said ratio is from about 2:1 to about 5:1.

8. A process according to claim 1 wherein said silicatungstic acid has the formula: $SiO_2.12WO_3$.

9. A process according to claim 1 wherein said silicatungstic acid is deposited on silica in an acid to silica weight ratio of about 5 to about 100 percent.

10. A process according to claim 9 wherein said ratio is about 30 to about 100 percent.

11. A process according to claim 1 wherein said liquid hourly space velocity ranges from about 0.1 to about 0.5 volume of feed per volume of catalyst per hour.

12. A process according to claim 1 wherein said temperature ranges from about 80° to about 120° C.

13. A process according to claim 1 wherein said pressure is ambient pressure.

14. A process according to claim 1 wherein said alcohol is ethanol.

15. A process according to claim 1 wherein said alcohol is propanol.